(12) United States Patent
Gruener et al.

(10) Patent No.: US 11,583,237 B2
(45) Date of Patent: Feb. 21, 2023

(54) METHOD AND MEASURING APPARATUS FOR AN X-RAY FLUORESCENCE MEASUREMENT

(71) Applicant: axiom insights GmbH, Hamburg (DE)

(72) Inventors: Florian Gruener, Hamburg (DE); Christoph Hoeschen, Magdeburg (DE); Florian Blumendorf, Hamburg (DE)

(73) Assignee: axiom insights GmbH, Hamburg (DE)

( * ) Notice: Subject to any disclaimer, the term of this patent is extended or adjusted under 35 U.S.C. 154(b) by 93 days.

(21) Appl. No.: 16/604,687

(22) PCT Filed: Apr. 6, 2018

(86) PCT No.: PCT/EP2018/058859
§ 371 (c)(1),
(2) Date: Oct. 11, 2019

(87) PCT Pub. No.: WO2018/189051
PCT Pub. Date: Oct. 18, 2018

(65) Prior Publication Data
US 2020/0155088 A1    May 21, 2020

(30) Foreign Application Priority Data
Apr. 11, 2017    (DE) .......................... 102017003517.2

(51) Int. Cl.
*A61B 6/00*    (2006.01)
(52) U.S. Cl.
CPC .......... *A61B 6/4241* (2013.01); *A61B 6/4275* (2013.01); *A61B 6/485* (2013.01)
(58) Field of Classification Search
CPC ..... A61B 6/4241; A61B 6/4275; A61B 6/485; G01N 2223/076; G01N 23/223
See application file for complete search history.

(56) References Cited

U.S. PATENT DOCUMENTS 4,599,741 A * 7/1986 Wittry ...................... G21K 1/06
378/45
4,882,780 A * 11/1989 Wittry ...................... G21K 1/06
378/85
(Continued)

FOREIGN PATENT DOCUMENTS

CN    1723388 A    1/2006
CN    1745296 A    3/2006
(Continued)

OTHER PUBLICATIONS

English translation of DE102012023344 (Year: 2014).*
(Continued)

*Primary Examiner* — Dani Fox
*Assistant Examiner* — Soorena Kefayati
(74) *Attorney, Agent, or Firm* — Caesar Rivise, PC

(57) ABSTRACT

A method and apparatus for x-ray fluorescence measurement in object (1) are disclosed. The method includes (a) producing x-ray beam (2) using source device (10), wherein beam extends through object parallel to a first projection direction, (b) irradiating object with beam at scan positions in first projection plane, which are set by scanning device (20) such that source device and object are moved relative to one another, (c) detecting x-ray radiation emitted from object using detector array device (30) securely connected to source device and including spectrally selective detector elements (31) arranged to detect radiation, and stop lamellas (32) extending in radial directions relative to beam direction shielding detector elements from radiation scattered in object and arranged such that detector elements are able to detect radiation from all locations, and (d) processing detector signals to capture x-ray fluorescence of target particles in radiation and to localize target particles in object.

15 Claims, 10 Drawing Sheets

(56) References Cited

U.S. PATENT DOCUMENTS

| | | | |
|---|---|---|---|
| 5,138,647 A * | 8/1992 | Nguyen | A61N 5/1049 378/65 |
| 5,570,239 A * | 10/1996 | Raimondi | F21V 11/02 359/873 |
| 6,448,559 B1 * | 9/2002 | Saoudi | A61B 6/037 250/370.11 |
| 7,313,221 B2 * | 12/2007 | Sowerby | G01N 23/09 250/269.4 |
| 7,672,422 B2 | 3/2010 | Seppi et al. | |
| 7,844,097 B2 * | 11/2010 | Wegener | H04N 19/152 382/239 |
| 8,971,488 B2 * | 3/2015 | Parham | A61B 6/583 378/85 |
| 9,207,195 B2 * | 12/2015 | Gozani | G01V 5/0016 |
| 9,775,572 B2 | 10/2017 | Katchalski et al. | |
| 9,947,117 B2 * | 4/2018 | Raupach | G06T 7/0012 |
| 2003/0031295 A1 * | 2/2003 | Harding | G01N 23/201 378/86 |
| 2004/0264628 A1 * | 12/2004 | Besson | G21K 1/10 378/5 |
| 2006/0034768 A1 * | 2/2006 | Schulz | G01N 23/223 424/9.42 |
| 2006/0171502 A1 * | 8/2006 | Schlomka | A61B 6/06 378/6 |
| 2006/0182217 A1 * | 8/2006 | Harding | A61B 6/485 378/44 |
| 2007/0172026 A1 * | 7/2007 | Schlomka | A61B 6/032 378/57 |
| 2008/0226025 A1 * | 9/2008 | Harding | G01N 23/223 378/44 |
| 2008/0230705 A1 * | 9/2008 | Rousso | A61B 5/4076 250/363.04 |
| 2008/0240342 A1 * | 10/2008 | Thran | G01T 1/171 378/19 |
| 2009/0118614 A1 * | 5/2009 | Sendai | A61B 8/4416 600/425 |
| 2009/0323899 A1 * | 12/2009 | Dorscheid | G21K 1/025 378/154 |
| 2011/0096897 A1 * | 4/2011 | Tonami | G21F 3/00 378/21 |
| 2011/0188629 A1 * | 8/2011 | Meng | G01N 23/223 378/45 |
| 2011/0255662 A1 * | 10/2011 | Shannon, Jr. | G01N 23/223 378/147 |
| 2011/0293068 A1 * | 12/2011 | Langhoff | G01N 23/2076 378/98.2 |
| 2012/0177182 A1 * | 7/2012 | Olesinski | G01N 23/04 378/87 |
| 2012/0265050 A1 * | 10/2012 | Wang | A61B 6/485 600/407 |
| 2015/0300966 A1 * | 10/2015 | Kessler | G01N 23/223 378/45 |
| 2016/0089091 A1 * | 3/2016 | Gagnon | A61B 6/4241 378/5 |
| 2016/0252471 A1 * | 9/2016 | Guo | G01N 23/223 378/45 |
| 2017/0043041 A1 * | 2/2017 | Wang | A61K 49/1824 |
| 2017/0265833 A1 * | 9/2017 | Danielsson | A61B 6/4291 |
| 2018/0052240 A1 * | 2/2018 | Tanabe | A61B 6/4241 |
| 2019/0008474 A1 * | 1/2019 | Sjolin | A61B 6/4291 |
| 2020/0132613 A1 * | 4/2020 | Krycki | G01N 23/223 |

FOREIGN PATENT DOCUMENTS

| | | | | |
|---|---|---|---|---|
| CN | 102625910 A | 8/2012 | | |
| CN | 102884422 A | 1/2013 | | |
| CN | 104853679 A | 8/2015 | | |
| CN | 106251295 A | 12/2016 | | |
| DE | 102004039048 A1 | 2/2006 | | |
| DE | 102012023344 A1 * | 6/2014 | | A61B 6/4291 |
| DE | 102012023344 A1 | 6/2014 | | |
| JP | 2011-505228 A | 2/2011 | | |
| WO | 2016082006 A1 | 6/2016 | | |

OTHER PUBLICATIONS

Bazalova et al., "Investigation of X-ray Fluorescence Computed Tomography (XFCT) and K-Edge Imaging", IEEE Transactions on Medical Imaging, vol. 31, No. 8, pp. 1620-1627 (2012).

Huo et al., "Sheet-beam geometry for in vivo fluorescent x-ray computed tomography: proof-of-concept experiment in molecular imaging", Optics Letters, vol. 33, No. 21, pp. 2494-2496.

Khrennikov et al., "Tunable All-Optical Quasimonochromatic Thomson X-Ray Source in the Nonlinear Regime", PRL, vol. 114, 195003 (2015).

Manohar et al., "Quantitative Imaging of Gold Nanoparticle Distribution in a Tumor-Bearing Mouse Using Benchtop X-ray Fluorescence Computed Tomography", Sci. Rep. 6, 22079; doi: 10.1038/srep22079 (2016).

English-language abstract of DE102012023344 (2019).

English-language version of the Written Opinion for PCT/EP2018/058859 dated Aug. 6, 2018.

English-language version of the International Search Report for PCT/EP2018/058859 dated Aug. 6, 2018.

West et al. (2012). Atomic spectroscopy update—X-ray fluorescence spectroscopy, J. Anal. At. Spectrom, 27(10) pp. 1603-1644.

* cited by examiner

METHOD AND MEASURING APPARATUS FOR AN X-RAY FLUORESCENCE MEASUREMENT

CROSS-REFERENCE TO RELATED APPLICATIONS

This application is a U.S. National Phase Application of PCT/EP2018/058859, filed Apr. 6, 2018, which claims priority from 102017003517.2, filed Apr. 11, 2017, the contents of which applications are incorporated herein by reference in their entireties for all purposes.

BACKGROUND OF THE INVENTION

The invention relates to a method for an X-ray fluorescence measurement, more particularly for X-ray fluorescence imaging, wherein it is detected, whether fluorescing target particles are present in an object to be examined, more particularly in the body of an examined test subject, and wherein target particles present in the object are localized. The invention relates also to an X-ray fluorescence measuring apparatus, more particularly an X-ray fluorescence imaging apparatus, for performing such a method. Applications of the invention exist in X-ray fluorescence imaging, more particularly for medical purposes and in this connection more particularly for objects with size scales as in respect of humans.

Tasks of medical imaging are the detection, characterizing and monitoring of pathological changes of the body being examined and/or the pharmacokinetics, whereby the distribution of medications in the body is measured in vivo. In order to improve these methods, techniques of what is known as "molecular imaging" are being developed, for example in order to allow early tumor diagnosis and better characterizing of the tumor tissue or pharmacokinetic examinations. In this connection the characterizing allows stratified approaches to treatment, in order thus to increase the chances of healing. Molecular imaging in medicine is aimed more particularly at the localization of biomarkers in the body, e.g. antibodies in the tumor tissue, and allows the in-vivo measurement of the distribution of medications in the body, in order to examine what proportion of the applied medication quantity is present in what place at what time. This could test the effectiveness of new medications more quickly already in the trial phase, as medications that are not present in sufficient quantity at the target site are unable to have a clinical effect.

To date, in the field of molecular imaging, positron emission tomography (PET) has been established, though as a nuclear medicine method it has crucial disadvantages for the patient. These include the relatively high dose, the exposure of unaffected organs, the short lifetime of radiopharmaceuticals, such that follow-up examinations require a new injection, the low spatial resolution at 4 to 6 mm, and the limited temporal resolution, such that relevant processes in tumor care or therapy cannot be examined. More particularly pharmacokinetic examinations over a longer period are thus effectively impossible. If medications are to be brought to the target site by drug carrier and released there, the "diagnostic time window" of PET is too short.

With X-ray fluorescence imaging (XRF imaging), which has been discussed for many years now as an alternative to PET, the disadvantages of PET can be avoided. In XRF imaging the biomarkers are bound e.g. to gold nanoparticles, which are excited by a scanning X-ray beam to emit X-ray fluorescence. The detecting of the X-ray fluorescence allows the localization of the biomarkers. Because the XRF imaging signal lies in narrowly limited energy ranges in the measured spectrum of the X-ray radiation emitted from the body, the detection of the biomarkers by means of an energy-selective detection of the X-ray fluorescence is supported. Conventional XRF imaging methods are however characterized by the disadvantages described below, such that to date they could only be tested on small-animal models (mice, small-animal phantoms) with relatively low sensitivity and with radiation doses much too high for medical applications, while there have been no examinations to date for examined objects of the size of a patient.

A main disadvantage of the XRF imaging method is that, in contrast to PET, it is not background-free and the amplitude of the background increases sharply with the size of the object being examined. Conventional XRF imaging methods would therefore have much too low a sensitivity in respect of large objects, such that these techniques would be out of the question for clinical use on patients. While the expected concentrations of e.g. gold nanoparticles are known from small-animal models (see e.g. N. Manohar et al. (2016) "Quantitative imaging of gold nanoparticle distribution in a tumor-bearing mouse using benchtop X-ray fluorescence computed tomography" in "Sci Rep" 6:22079), such XRF imaging methods could not detect these gold nanoparticle quantities in the human, because the sensitivity would then no longer be sufficient.

The XRF imaging background grows with the size of the object, because at the same time the probability increases, that the irradiated X-ray photons experience multiple Compton scatterings. As a result of the scatterings the energy of the photons can be reduced, such that the scattered photons are detected in the same energy range as the fluorescence photons. Because these cannot be distinguished as signal photons from the background photons in the common energy range, the sensitivity of the detection of biomarkers is limited. Without a reduction in the background e.g. 1000 signal photons can be lost in a background in the questionable XRF imaging energy range of around 1 million photons, as the signal would not be statistically significant. To date, to reduce the XRF imaging background, collimator geometries have been proposed, the functioning of which however requires advance information on where the volume with the enriched contrast agent lies in the object. Furthermore, conventional collimators restrict the field of view of the detector elements, as a result of which signal is lost, which can be compensated for only by means of a higher dose of radiation.

Finally, X-ray fluorescence imaging has been examined to date only either on large synchrotron installations or with conventional compact X-ray tubes. However neither method is suitable for clinical applications, as synchrotron installations are too large and conventional X-ray tubes typically emit radiation with too large a divergence and/or too low an intensity in rays with small divergence and have too large an energy bandwidth.

Described in DE 10 2012 023 344 A1 is the X-ray fluorescence analysis of a contrast agent dispersion in an object using a collimated X-ray source filtered in the lower energy range. Here the X-ray radiation generated through X-ray fluorescence is separated with collimator leaves from multiply scattered X-rays and thereafter measured energy-selectively with monochromator crystal layers and an X-ray detector. Through rotation and displacement of the measuring apparatus about the object a computerized tomography imaging is facilitated. Although a medical imaging on large objects is to be achieved with the technique according to DE 10 2012 023 344 A1, application in practice is limited owing to the following disadvantages. Firstly, with the monochromator crystal layers only fluorescence photons emitted perpendicular to the excitation beam direction can be detected, as the Bragg condition for reflection on the monochromator crystals is not fulfilled for any other directions. That means more particularly that a photon that is emitted e.g. at the start of the beam volume in the object, though not perpendicular to the beam direction, can pass through the leaves, but is not reflected on the monochromator crystals, because the Bragg condition is not fulfilled from this photon direction. Thus this photon, even though it is a signal photon, does not contribute to the measured signal, such that the technique described in DE 10 2012 023 344 A1 is extremely inefficient. Secondly, owing to the low signal yield there is a substantial disadvantage due to a low signal-to-noise ratio. The objective of the invention is to provide an improved method for X-ray fluorescence measurement, more particularly for X-ray fluorescence imaging, and/or an improved X-ray fluorescence measuring apparatus, with which disadvantages of conventional techniques are avoided. The invention should more particularly make it possible to detect the X-ray fluorescence of target particles in an object with an increased sensitivity, to suppress the background more efficiently, to lower the radiation intensity and/or to improve the spatial resolution. The invention should moreover more particularly allow the previously impossible examination of larger objects and facilitate a clinical X-ray fluorescence imaging, more particularly on humans.

These objectives are achieved by means of a method for X-ray fluorescence measurement and an X-ray fluorescence measuring apparatus of the invention.

BRIEF SUMMARY OF THE INVENTION

According to a first general aspect of the invention the aforementioned objective is achieved by means of a method for X-ray fluorescence measurement, wherein the presence of fluorescing target particles is detected in an object to be examined and any target particles that might be present are localized in the object in at least one projection plane (hereinafter: first projection plane).

By means of a source device an X-ray beam is generated, which is directed through the object in an X-ray beam direction parallel to a first projection direction. The X-ray beam is preferably a needle beam (pencil beam) having a constant diameter or a small divergence (e.g. ≤1 mrad). The diameter of the X-ray beam defines the spatial resolution of the XRF imaging method and is therefore preferably at least 0.1 mm, more particularly at least 0.2 mm, and/or at most 1 mm, more particularly at most 2 mm.

The object is irradiated (scanned) with the X-ray beam at a multiplicity of scan positions in the first projection plane. The scan positions (positions at which irradiation takes place) are set by a scanning device, by means of which the source device and the object are moved relative to one another. For each scan position the X-ray beam intersects the first projection plane at different coordinates. Preferably the X-ray beam is orientated perpendicular to the first projection plane. The scan positions are distributed in the first projection plane e.g. row-wise and column-wise as matrix.

At each scan position the X-ray radiation, emitted from the object in a plurality of spatial directions, is detected using a detector array device, which is securely connected to the source device. By means of the scanning device the source and detector devices and the object are moved relative to one another. Preferably the source and detector devices are moved relative to a stationary-mounted object.

The detector array device has an arrangement of spectrally selective detector elements (referred to also as pixels), which are distributed in a plurality of various spatial directions around the object. The detector elements are arranged along an array surface, which is curved, curved in sections and/or made up of flat component surfaces. For each scan position an energy spectrum of the detected X-ray photons exiting the object is measured with each spectrally sensitive detector element and these individual spectra can be combined into a sum energy spectrum of selected and/or all detector elements. The measurement of energy spectra with the detector elements presents an essential difference from DE 10 2012 023 344 A1, where the detector can measure only signal photons having a certain energy and emitted perpendicular to the X-ray beam direction. Furthermore the formation of sum energy spectra (sum signals) has more particularly the advantage over the consideration of the spectra of the individual detector elements, that in the case of the small quantities of target particles expected, e.g. from the above-cited small-animal model, the number of the signal photons in the individual detector elements would be so small, that any determination of the significance would be made difficult or even ruled out.

The detector elements are arranged for the detection of the X-ray radiation in the plurality of spatial directions. The "detector element" can be an individual, spectrally-resolving detecting element, a combination of multiple (e.g. 4×4) detecting elements or a detecting component made up of multiple detecting sub-elements. The combination of multiple detecting elements can more particularly have advantages for the statistics of the detected X-ray photons. The component consisting of sub-elements can more particularly have advantages for the spectrally-resolving detection in the use of a laser-based Thomson source as source device, as in this connection the photons are detected almost simultaneously and one ensures by means of the sub-elements, that no more than 1 photon per detector time window is detected per sub-element.

The detector array device has moreover a plurality of screen lamellas, which extend between the object and the detector elements in radial directions relative to the X-ray beam in the object, shield the detector elements from X-ray radiation scattered in the object singly or multiply, more particularly outside the X-ray, and are arranged in such a way that the detector elements are able to detect X-ray radiation from all locations within the volume of the X-ray beam in the object. More particularly each individual detector element can detect X-ray radiation from all locations within the volume of the X-ray beam in the object. The screen lamellas are arranged such that free (unblocked) sight-lines extend from the entire volume of the X-ray beam in the object to the detector elements and sight-lines from the other, not directly irradiated volume in the object to the detector elements are blocked by the screen lamellas. The screen lamellas can preferably be flat leaves, each with a constant thickness, or alternatively have thickness gradients, which taper towards the beam. Because of the finite size of the lamellas a small proportion of the signal photons is absorbed, which is however negligible as an error in the X-ray fluorescence measurement, as the proportion of the absorbed signal photons is preferably less than 10%.

The screen lamellas advantageously provide a first contribution to the background reduction through shielding of the scattered radiation from the volume of the object outside the volume currently irradiated at the scan position.

Detector signals of the detector elements are processed, in order to detection X-ray fluorescence of target particles in the detected X-ray radiation and in order to localize the target particles in the object in the event of detection of the X-ray fluorescence. To this end according to the invention a subset of detector elements is identified (known as significant or identified detector elements) for each of a multiplicity of predetermined scan positions, the detector signals of said detector elements facilitating the detection of the X-ray fluorescence of the target particles with a statistical significance that is increased in comparison with the remaining detector elements. The group of the significant (or: identified) detector elements is sought e.g. respectively for each scan position or only for a selection of scan positions (e.g. every second scan position in the matrix of scan positions). In this connection more particularly the significance of a sum signal (sum spectrum) of the detector elements (i.e. of the identified subset) is compared with the significance of the sum signal (sum spectrum) of each other subset of the detector elements.

If significant detector elements are found at at least one scan position, based on the detector signals of the significant detector elements and without taking into account the detector signals of the remaining detector elements, the presence of target particles and this scan position, for which the significant detector elements are found, are established as at least one target scan position. The target scan position represents the coordinates in the first projection plane, at which the target particles are localized. Otherwise, if significant detector elements are identified at no scan position, it is detected that no target particles are detectable in the object.

The selection of the significant detector elements provides a substantial, advantageously the greatest, contribution to background reduction. This aspect of the invention is based more particularly on the close examination, by the inventors, of the intrinsic background that is created by multiple Compton scattering of the irradiated photons in the body. Crucial for the reduction of the background is the finding that the background is direction-dependent, i.e. anisotropic whereas the fluorescence signal of the target particles is emitted isotropically, i.e. does not distinguish any direction. In other words, the inventors have found that the background-X-ray radiation has a non-uniform special distribution (anisotropy) owing to the multiple Compton scattering, more particularly in respect of large objects as in clinical applications. At scan positions at which the X-ray beam hits target particles and X-ray fluorescence is created, the detector elements of the detector array device detect the X-ray fluorescence in various spatial directions (relative to the X-ray beam direction) with a different background in each case. By the seeking of the significant detector elements those detector elements are detected, the X-ray fluorescence sum spectrum of which is detected with a relatively low background signal in comparison with the remaining detector elements. As a result the quantitative finding of the anisotropy of the intrinsic background is transformed into a reduction of the background with the help of direction-dependent detection.

The inventors have found more particularly that the anisotropy of the photons, which have an energy in the signal energy range owing to the multiple Compton scattering, is dependent on the energy of the X-ray photons used for excitation. The X-ray photons used for excitation have preferably an energy, at which the anisotropy is at its maximum. Advantageously this facilitates a particularly effective suppression of the background. The energy at which the anisotropy is at its maximum can be determined through experimental tests (e.g. on a phantom) or numerical simulations. Particularly preferably the energy of the photons of the exciting X-ray beam is chosen in a narrow energy interval above the K edge of the fluorescing element in the target particles, in the case of gold target particles at about 85 keV.

With the help of computer simulations the inventors were able to show that the background can be reduced by a factor of about 600 to 1000—with a correspondingly effective increase in significance and in fact using a test phantom with a diameter of 30 cm and a minimum dose, thus satisfying the requirements for imaging on humans. Advantageously in clinical applications, e.g. in tumor diagnosis, small quantities of test particles can thus be detected in objects, e.g. humans. This is achieved by both signal and background being measured only in certain directions, i.e. more particularly with the help of the sum spectrum of the identified detector elements. As is evident, these directions form only e.g. approx. 30% to 40% of the total solid angle. This restriction is however the key to the effective increase in significance. Only the increase in significance achieved according to the invention allows the sensitivity required in medical imaging on humans.

The method according to the invention differs from all conventional XRF imaging methods, in which measuring is usually done only in one direction (usually 90 degrees and more to the direction of irradiation) and/or collimators always allow only the observation of a section of the beam volume. A quantitative examination by way of the individual contributions of all directions to the overall significance of the fluorescence signal for the detection along the entire beam volume has not been known to date. More particularly, in comparison with the technique according to DE 10 2012 023 344 A1, a considerably improved yield of detection of fluorescence photons from all spatial directions and a detection with sharply reduced background signal is achieved, in order thereby to achieve a significantly higher efficiency of the method with regard to dose and irradiation time.

The inventors have found further that an isotropic detection in all spatial directions, in which one would expect a maximum fluorescence signal, would at the same time produce a maximum background detection. The resulting significance of the fluorescence signal would then be so small that, more particularly in respect of objects of the size of human test subjects, one would only be able to measure quantities of e.g. gold nanoparticles of such a size that they are medically irrelevant. That notwithstanding it is proposed in the invention, to select the spatial directions, in which X-ray radiation is detected, a priori through the selection of the significant detector elements. Numerical analyses of the inventors have shown for example that a detection provides a considerable background reduction in approx. 40% of all possible spatial directions. The quantitative examination of the anisotropy of the Compton background in respect of large objects, performed for the first time by the inventors, provided more particularly the underlying concept of the invention, to measure only a sum signal from significant (identified) detector elements in X-ray fluorescence measurement.

The invention allows such a sharp reduction in the intrinsic background that X-ray fluorescence imaging becomes usable on humans as imaging modality in clinical practice. Whereas the achievable sensitivities of conventional techniques such as CT and MRT are too low, in order to function as early tumor diagnosis, the X-ray fluorescence measurement according to the invention allows a significant increase in sensitivity, whilst at the same time avoiding the aforementioned disadvantages of PET imaging. The invention makes it possible to quantify the increase in sensitivity. Thus the potential of X-ray fluorescence imaging can be called quantitatively characterized in comparison with the other imaging modalities.

According to a second general aspect of the invention the aforementioned objective is achieved by means of an X-ray fluorescence measuring apparatus, which is configured to localize fluorescing target particles in an object to be examined and comprises a holding device to accommodate the object, a source device to generate an X-ray beam, which extends through the object to be examined in an X-ray beam direction parallel to a first projection direction, a detector array device to detect X-ray radiation, emitted from the object in a plurality of spatial directions, a scanning device, by means of which the source and detector array devices and the holding device can be moved relative to one another, and a control device to receive and process detector signals of the detector array device. Preferably the X-ray fluorescence measuring apparatus is designed for performing the method according to the first general aspect of the invention.

The source device is preferably a compact laser-based Thomson source (X-ray radiation source, which generates X-ray radiation based on the Thomson scattering of laser light on relativistic electrons), e.g. as described by K. Khrennikov et al. ("Tunable All-Optical Quasimonochromatic Thomson X-ray Source in the Nonlinear Regime") in "Phys. Rev. Lett.", Vol. 114, p. 195003 (2015), but it can also comprise a synchrotron source or generally an X-ray source, e.g. X-ray tube, which generates X-ray radiation with sufficiently low divergence and high intensity more particularly in the energy range above the K edge of the element of the target particles. The detector array device is fixedly connected to the source device, and it has a multiplicity of spectrally selective detector elements and a plurality of screen lamellas, as described above with reference to the first aspect of the invention. With the scanning device firstly the source and detector array devices and secondly the holding device can be moved relative to one another, such that the X-ray beam can scan the object in the first projection plane at a multiplicity of scan positions.

The control device (referred to also as computing device, evaluation device or control and evaluation device) is configured to identify a subset of significant detector elements for each of a multiplicity of predetermined scan positions, the detector signals, more particularly sum signal, preferably sum spectrum, of said detector elements facilitating the detection of the X-ray fluorescence of the target particles with a statistical significance that is increased in comparison with the remaining detector elements, and, if significant detector elements are found at at least one scan position, to detect the presence of target particles and to establish this scan position as target scan position, at which the target particles are localized in the first projection plane, or, if detector elements are found at no scan position, to detect that no target particles are detectable. The control device is e.g. a computer, on which a program for performing the processing of the detector signals runs or which is configured as special computer for performing the processing of the detector signals. The control device is coupled with the components of the X-ray fluorescence measuring apparatus, in order for example to control the source, scan and detector array devices or to receive signals from the same.

According to a preferred application of the invention in X-ray fluorescence imaging the examined object is a human or animal test subject or a body part of the same. The target particles were supplied to the test subject beforehand, e.g. through oral or other administration or injection. A preparatory step with a supply of target particles, more particularly through injection into the body of the test subject, is not part of the invention. Alternatively other, non-biological objects can be examined. The target particles comprise particles, more particularly nanoparticles, which are suitable for exciting X-ray fluorescence with irradiated photons, more particularly with an energy of at least 15 keV, and have preferably a mass number in the range of the mass numbers of iodine to gold. These elements have the advantage that the K-shell fluorescence photons have a sufficient transmission in the body of the test subject, such that the target particles are detectable at any depth (in contrast to optical fluorescence). Furthermore the target particles are functionalized with a marker substance. The marker substance (or biomarker) comprises a substance that binds specifically to parts of the examined object, e.g. to predetermined cells or cell groups or to predetermined tissue, e.g. tumor cells or tissue. The target particles can however also be functionalized with medications, in order thus to allow in-vivo pharmacokinetic examinations.

The presence of fluorescing target particles in the object to be examined means that target particles introduced beforehand, e.g. taken orally or otherwise or injected, have been enriched in at least one sub-region of the examined object through the specific binding. The detecting of the presence of target particles comprises the detecting of an enrichment (concentration) of the target particles in the at least one sub-region, e.g. on tissue or cell groups. The localization of the target particles comprises the detection of the site of the enrichment at least in relation to the first projection plane, preferably however in relation to all three spatial dimensions. The invention has more particularly the following advantages for medical applications. The intrinsic background in medical X-ray fluorescence imaging can be reduced so sharply that, with an acceptable radiation dose, minimal quantities of functionalized gold nanoparticles can be detected in the body, in order thus to make possible e.g. an early tumor diagnosis.

According to a preferred embodiment of the invention the subset of the significant detector elements is sought after for each of the multiplicity of predetermined scan positions, such that the detector signals, more particularly sum signals, of the significant detector elements facilitate the detection of the X-ray fluorescence of the target particles with a maximum statistical significance. The control device is configured to select the detector elements, from the detector signals sum signal of which the sought-after X-ray fluorescence of the target particles can be detected with maximum statistical significance. Advantageously the maximum sensitivity of the X-ray fluorescence measurement is thus achieved. In this connection maximum sensitivity means more particularly that any other subset of detector elements has a sum signal with less significance of the signal.

Advantageously various methods are available for identifying the subset of the significant detector elements. According to a first preferred variant a single-stage method is provided, in which the detector signals of the detector elements are subjected stepwise to an analysis of the appearance of the sought-after X-ray fluorescence of the target particles at the considered scan position, preferably with the control device, whereby the statistical significance of the X-ray fluorescence in the sum signal of the detector signals of the considered detector element and of the remaining detector elements is examined. Those detector elements are discarded, the detection signals of which do not deliver any increase of the statistical significance of the sum signal of the remaining detector elements. All detector elements not discarded form the group of the significant detector elements. The single-stage method has more particularly the advantage that the significant detector elements can be established with high process speed.

According to a second preferred variant a two-stage method is provided, in which in a first selection step detector elements are discarded, which detect predominantly background X-ray scatter radiation, and in a second selection step further detector elements are discarded, the detection signals of which do not deliver any increase of the statistical significance of a sum signal of the remaining detector elements. The detection of the detector elements that detect predominantly background X-ray scatter radiation in the first selection step is based on the spectrally selective detection with the detector elements. (Background) energy ranges in which only background photons can appear are used as reference for assessment of the (fluorescence) energy ranges, in which both background photons and fluorescence photons can appear. If the detector signal of a considered detector element provides an amplitude in the background energy range that does not differ significantly statistically from the signal amplitude in a pure background energy range, more particularly is significantly greater than the expected signal amplitude (in the fluorescence range), the detector element is detected as detecting predominantly background X-ray scatter radiation and therefore discarded. The two-stage method performed preferably with the control device has more particularly the advantage that the significant detector elements can be established with precision and reproducibility.

Advantageously the aforementioned variants can be combined more particularly with a preselection, in which for each of the multiplicity of predetermined scan positions an initial subset of detector elements is preselected, which is established beforehand on the basis of a priori information (advance information) about the examined object, whereby the subset of the significant detector elements to be identified is sought after inside the preselected initial subset. The a priori information can be based e.g. on numerical simulations, experimental simulations, existing images of the object, e.g. patient images from CT or MRT examinations, and/or an already known localization of the target particles, e.g. a disease localization (e.g. a hepatic tumor) or as target volume for pharmacokinetic examinations. Advantageously the selection of the significant detector elements is simplified with consideration of the initial subset and the process speed is elevated.

According to a further advantageous embodiment of the invention the X-ray fluorescence measurement takes place in two stages with a preparatory measurement and a main measurement, in which the method according to the invention is performed using an X-ray beam in each case with a first, larger, and a second, e.g. smaller, diameter with different local resolution. However the first beam does not necessarily have to be larger. It can be just as large as the second beam, though less dose is applied and thereafter adjacent pixels are added up, in order to obtain sufficient data for the statistical evaluation. This variant has the advantage that the data of the preliminary scan can be used further for the second measurement. In the preparatory measurement a preparatory target scan position representing a target scan region in the first projection plane is established with the first X-ray beam with the first diameter, if the presence of the target particles is detected. In the main measurement with the second X-ray beam with the second diameter the sought-after target scan position is established inside the target scan region. Advantageously the preparatory measurement can be used, in order to discover with great speed, whether target particles are detectable in the object and in what target scan region they might be localized. If no X-ray fluorescence of target particles is detected, the main measurement can be omitted. If X-ray fluorescence of target particles is detected, the main measurement provides the precise localization of the target particles, whereby the time taken for the main measurement can be reduced through restricting solely to the target scan region ("zooming" into the target region).

The detector array device can completely surround the object with the exception of solid-angle regions to radiate the X-ray beam through an irradiation window and optionally to introduce the object into the detector array device through an introduction window ($4\pi$ detector). The irradiation window has a small lateral dimension, which is adapted to the diameter of the X-ray beam. The introduction window has a lateral dimension that depends on the shape and size of the object and optionally parts of the holding device. Advantageously almost all X-ray photons from the object are detected therewith.

According to an alternative embodiment of the invention the detector array device comprises an arrangement of the detector elements on a surface that covers only, more particularly approximately, a half-space in forward direction of the X-ray beam. The inventors have found that the significant detector elements are found predominantly in the half-space in forward direction. Advantageously this embodiment of the invention makes possible a simplified set-up of the detector array device and a simplified access to the object being examined.

According to a further preferred embodiment of the invention the detector array device can comprise an arrangement of the detector elements along a spherical surface and/or a cylindrical surface. In this case the radial arrangement of the screen lamellas is simplified.

The localization of the target particles in the first projection plane generally already provides evaluable image information about the object being examined and the position of the target particles in the same. For completed imaging, according to a particularly preferred embodiment of the invention, a swivelling of the source and detector array devices relative to the object is provided after the localization of the target particles in the first projection plane in such a way that in the swivelled state the X-ray beam extends through the object parallel to a second projection direction, which deviates from the first projection direction. To perform the swivelling, the X-ray fluorescence measuring apparatus is provided with a swivel device, with which the source and detector array devices, preferably together with the scanning device, are swivellable relative to the holding device of the object, such that the X-ray beam extends parallel to the second projection direction.

In the swivelled state a further irradiation of the object with the X-ray beam takes place at a multiplicity of scan positions, which in this case is limited to a scanning line in a second projection plane, which deviates from the first projection plane, whereby the scanning line contains the previously established target scan position, and a detection of the position of the target particles along the scanning line, preferably with the control device. With the site information about the scan position in the first projection plane and the scan position on the scanning line in the second projection plane the position of the target particles in the object is completely characterized.

The second projection direction is generally not parallel to the first beam direction, i.e. it must only allow the scan directions to be able to intersect each other in space, whereby this intersection point then marks the localization of the target particles, if the two scan directions each display a signal. According to a preferred variant of the invention however it is provided that the swivelling of the source and detector array devices takes place, such that the second projection direction is orientated perpendicular to the first projection direction and the second projection plane is orientated perpendicular to the first projection plane.

According to a further preferred embodiment of the invention a taking of at least one absorption projection image of the object can be provided. Advantageously the detector elements in this case fulfil a double function to detection the X-ray fluorescence and to detection a conventional X-ray absorption image, e.g. to establish anatomical information about an examined test subject. Preferably the absorption projection image is combined with the target scan position in the first projection plane or the complete characterizing of the target position in the space, in order to obtain an object image e.g. for a subsequent diagnosis.

BRIEF DESCRIPTION OF THE DRAWINGS

Further details of the invention are described below with reference to the accompanying drawings, which show in.

DETAILED DESCRIPTION OF PREFERRED EMBODIMENTS

Embodiments of the invention are described below with reference to the features of the X-ray fluorescence measuring apparatus and of the method more particularly for the detecting of the presence of fluorescing target particles in an object to be examined and, if target particle fluorescence is detected, for localization of the target particles. Details of the X-ray fluorescence measuring apparatus, e.g. details of the source device, the scanning device, the detector elements or the swivel device can be realized, as known per se from corresponding mechanical, electrical or X-ray optical components of conventional techniques, so they are not described here in detail. For applications in medical imaging the X-ray fluorescence measuring apparatus can be provided with further components, as known per se from conventional techniques, e.g. a drive to actuate a holding device, operating devices, a display device and the like.

By way of example reference is made to embodiments, in which the source and detector array devices are moved relative to the stationary-positioned object for the setting of the scan positions. The invention is usable correspondingly, e.g. in respect of stationary sources such as conventional synchrotron sources, such that the object is moved relative to stationary-positioned source and detector array devices.

Figure 4:
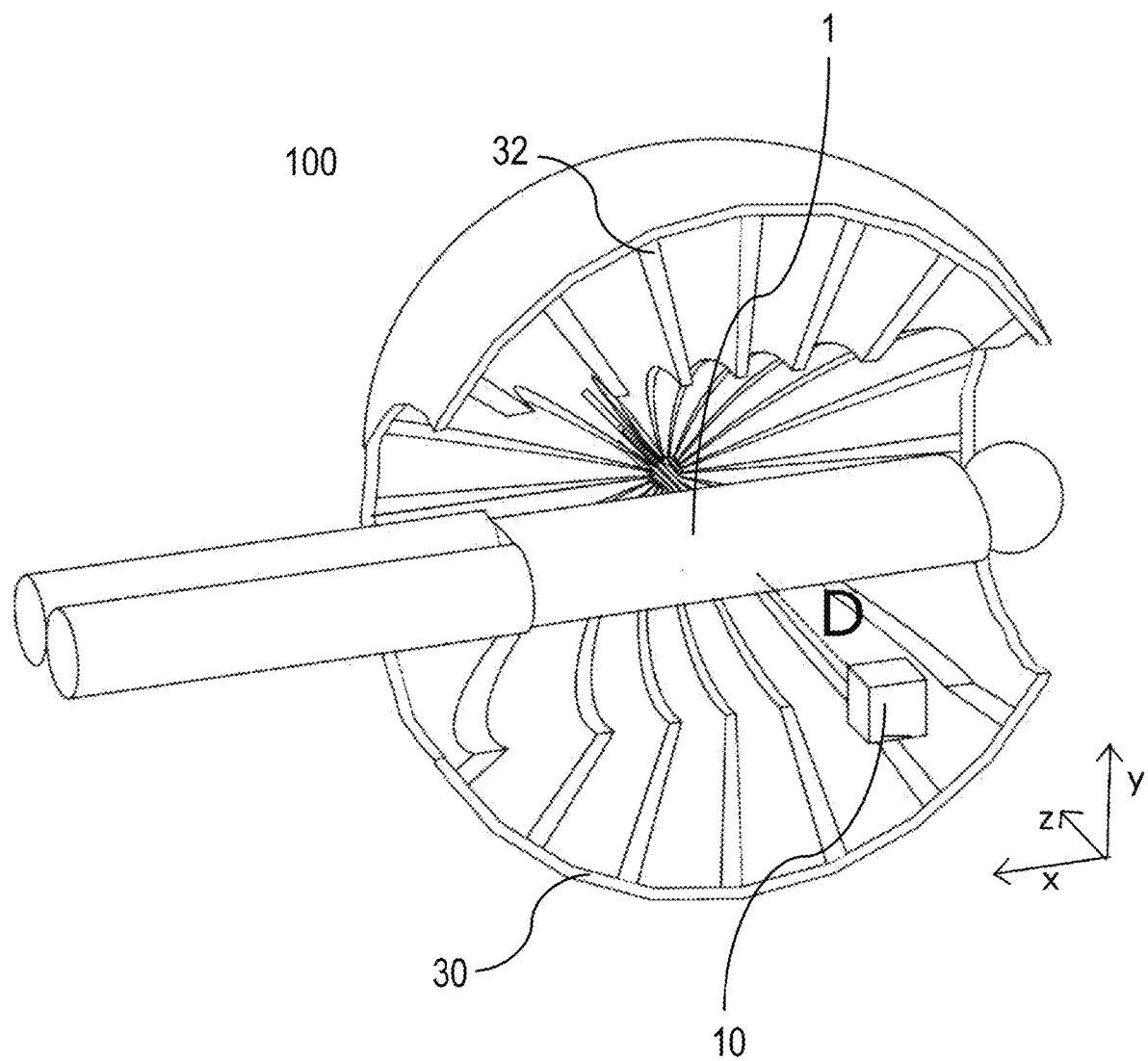
Figure 5:
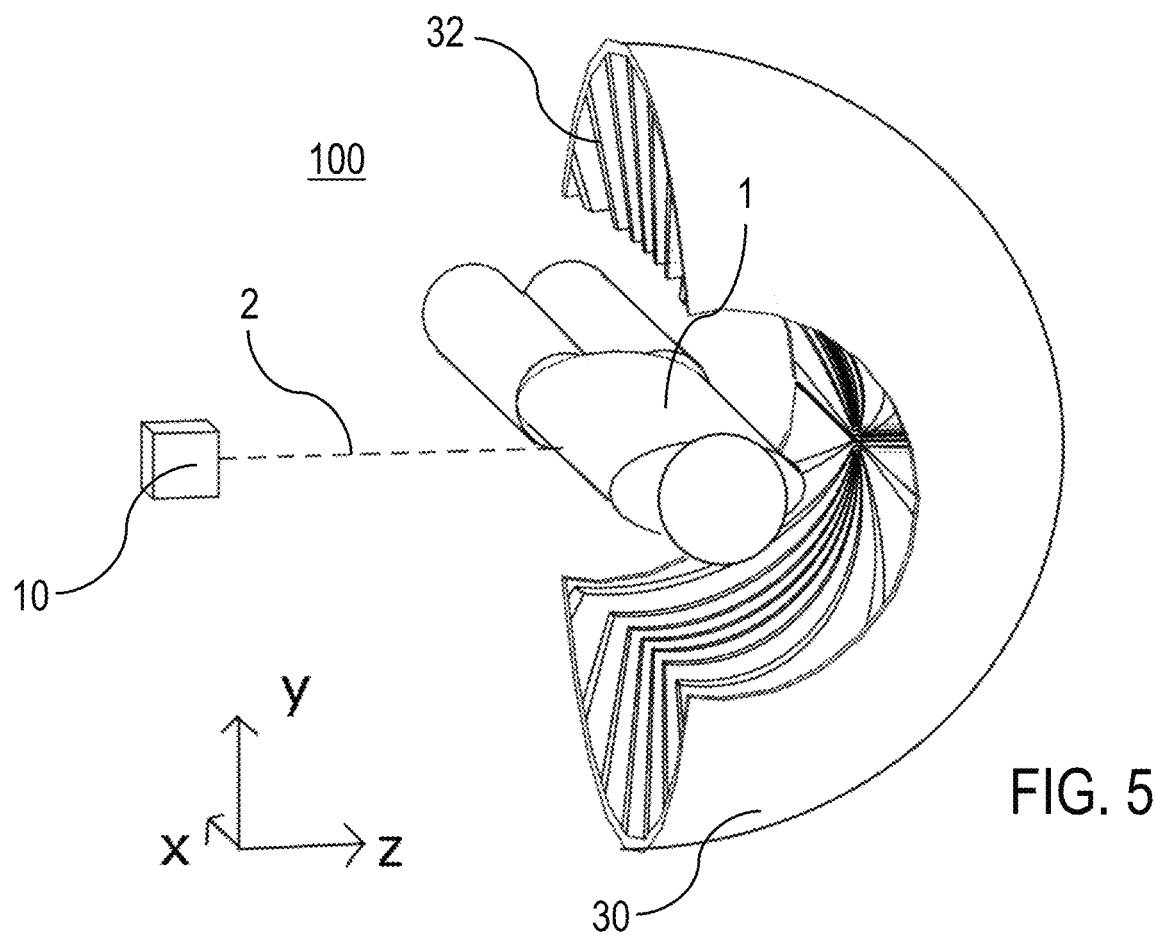
Figure 6:
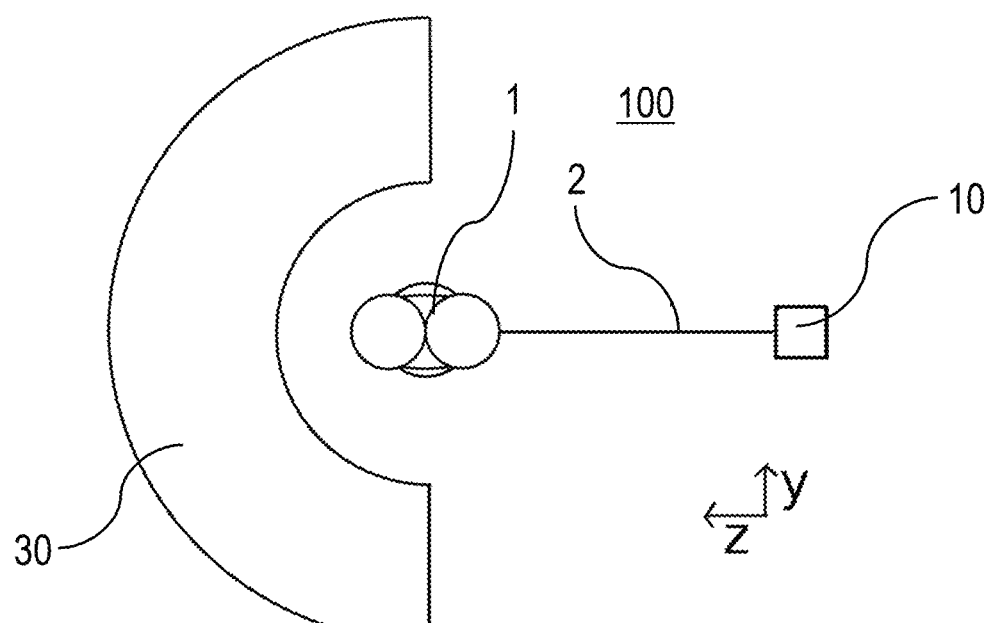

FIGS. 1 to 6 schematically show different perspectives of the X-ray fluorescence measuring apparatus 100 with an arrangement of detector elements 31 (one detector element is shown by way of example) on a spherical surface, whereby the arrangement of the detector elements 31 surrounds the object almost completely (FIGS. 1 to 3) or only in a half-space in forward direction of the X-ray beam (FIGS. 4 to 6).

Figure 1:
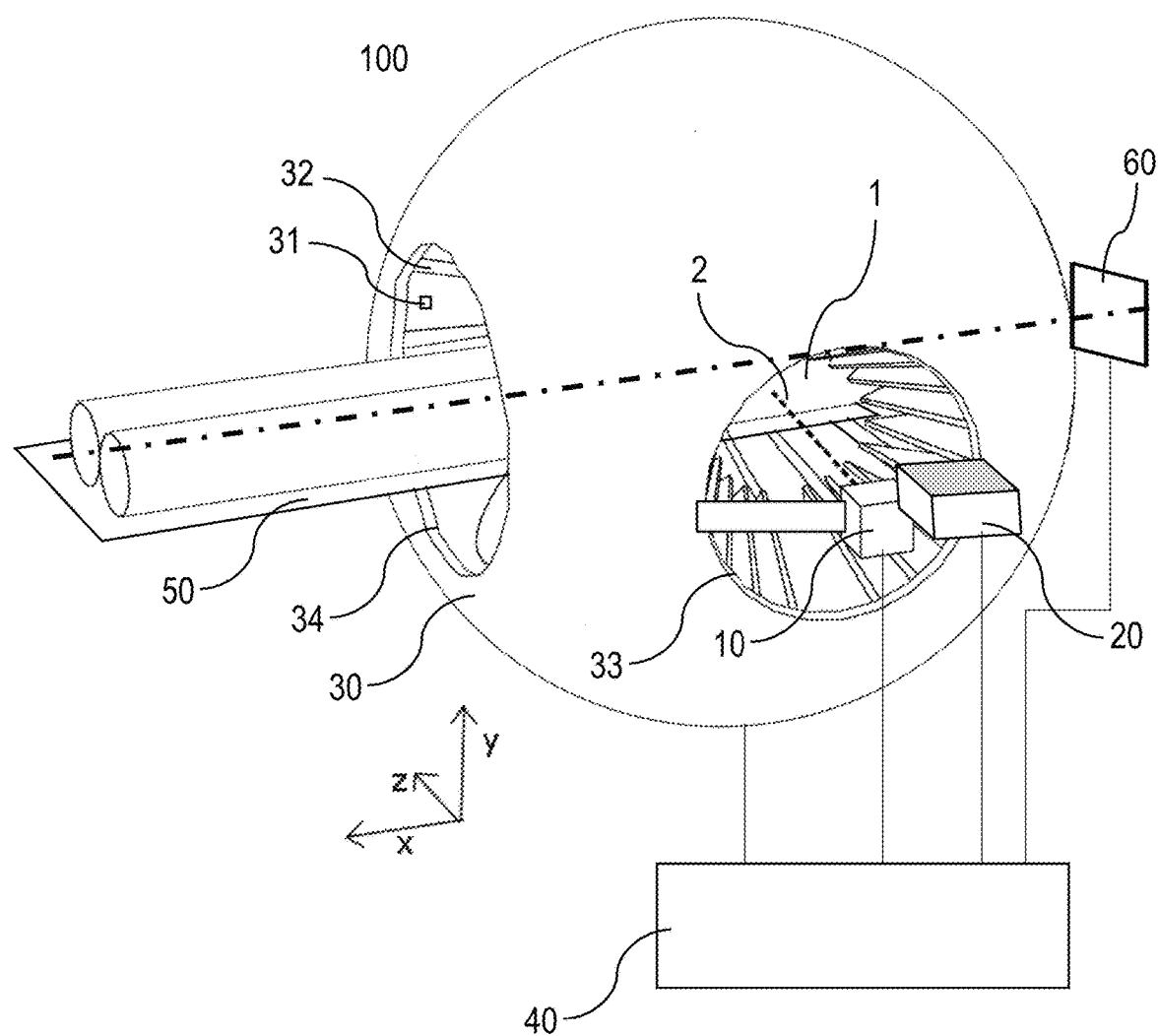
FIGS. 1 to 6: schematic views of preferred embodiments of the X-ray fluorescence measuring apparatus according to the invention with an arrangement of detector elements on a spherical surface.
Figure 2:
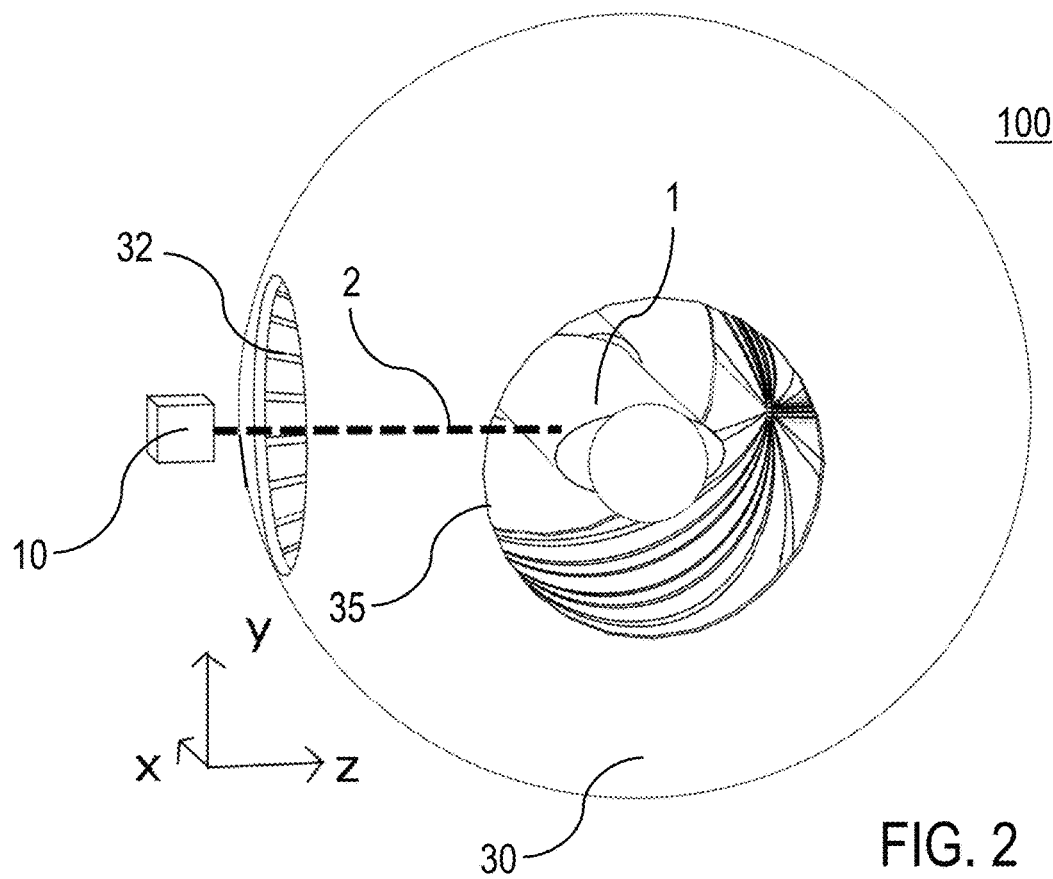
Figure 3:
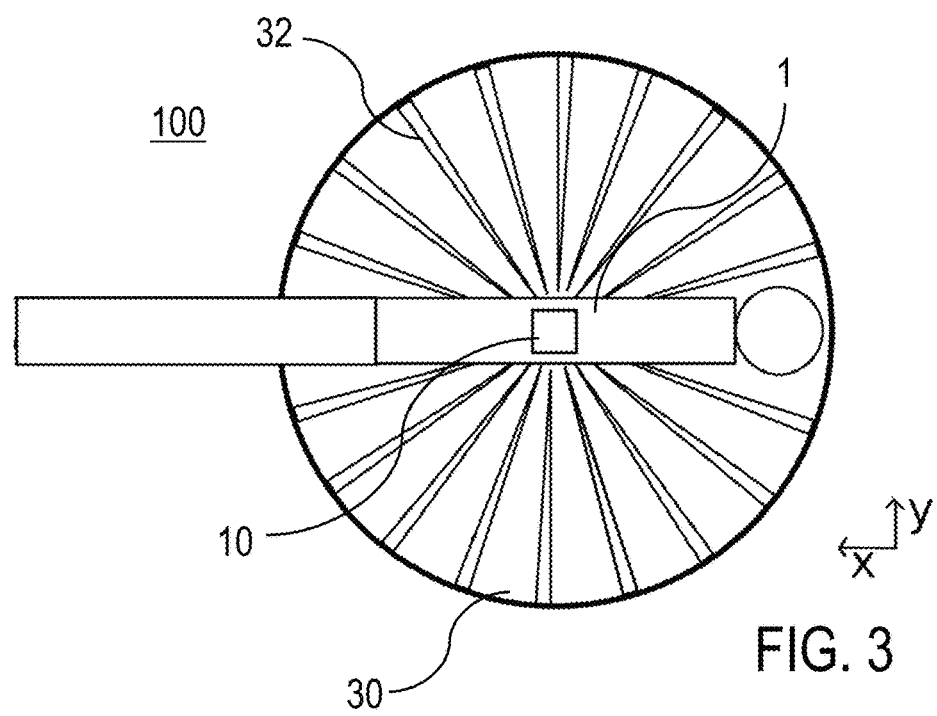

According to FIG. 1 the X-ray fluorescence measuring apparatus 100 comprises respectively a holding device 50, e.g. a couch, to accommodate the object 1, e.g. a schematically shown patient, a source device 10 to generate an X-ray beam 2 in a first projection direction (z direction), a scanning device 20, a detector array device 30, which is securely connected to the source device 10 (shown schematically only in FIG. 1), a control device 40 to receive and process detector signals of the detector array device 30 and an optionally provided swivel device 60. With the scanning device 20, which preferably contains a mechanical drive with a servomotor, the source and detector array devices 10, 30 can be moved row-wise and column-wise parallel to the first projection plane (x-y plane), such that the X-ray beam 2 is scanned through the object 1 perpendicular to the first projection plane. With the swivel device 60 the source and detector array devices 10, 30 can be rotated together with the scanning device 20, such that the X-ray beam is directed in a second projection direction (e.g. negative y direction). In the remaining FIGS. 2 to 6 the holding device, the scanning device, the control device and the swivel device are not shown, but are provided as represented in FIG. 1.

The source device 10 is e.g. a source of the type laser-based Thomson source. The detector array device 30 has the form of a hollow sphere with an internal diameter of e.g. 120 cm, on the inner surface of which are arranged the detector elements 31 and between these, projecting into the hollow sphere, screen lamellas 32. The hollow sphere is a full sphere (FIGS. 1 to 3) or a hemisphere (FIGS. 4 to 6). The detector elements 31 and the screen lamellas 32 are shown schematically. In practice the number and size of the detector elements and the number, size and orientation of the screen lamellas 32 are selected depending on the specific measuring task. The detector elements 31 are configured for the detection of spectra of the X-ray radiation emitted in the object 1; they comprise e.g. detector elements of the type CdTe (manufactured e.g. by Amptek). The screen lamellas 32 are plates with a thickness that decreases towards the widening of the volume irradiated in the object, i.e. towards the X-ray beam 2 (see schematic sectional representation in FIG. 3) or planar diaphragms. The screen lamellas 32 consist for example of molybdenum. E.g. up to 3600 screen lamellas 32 are provided. The detector array device 30 has further two openings, comprising an irradiation window 33 and an introduction window 34 for the holding device 50 with the object 1. Additionally a further access window 35 can be provided (see FIG. 2).

Figure 7:
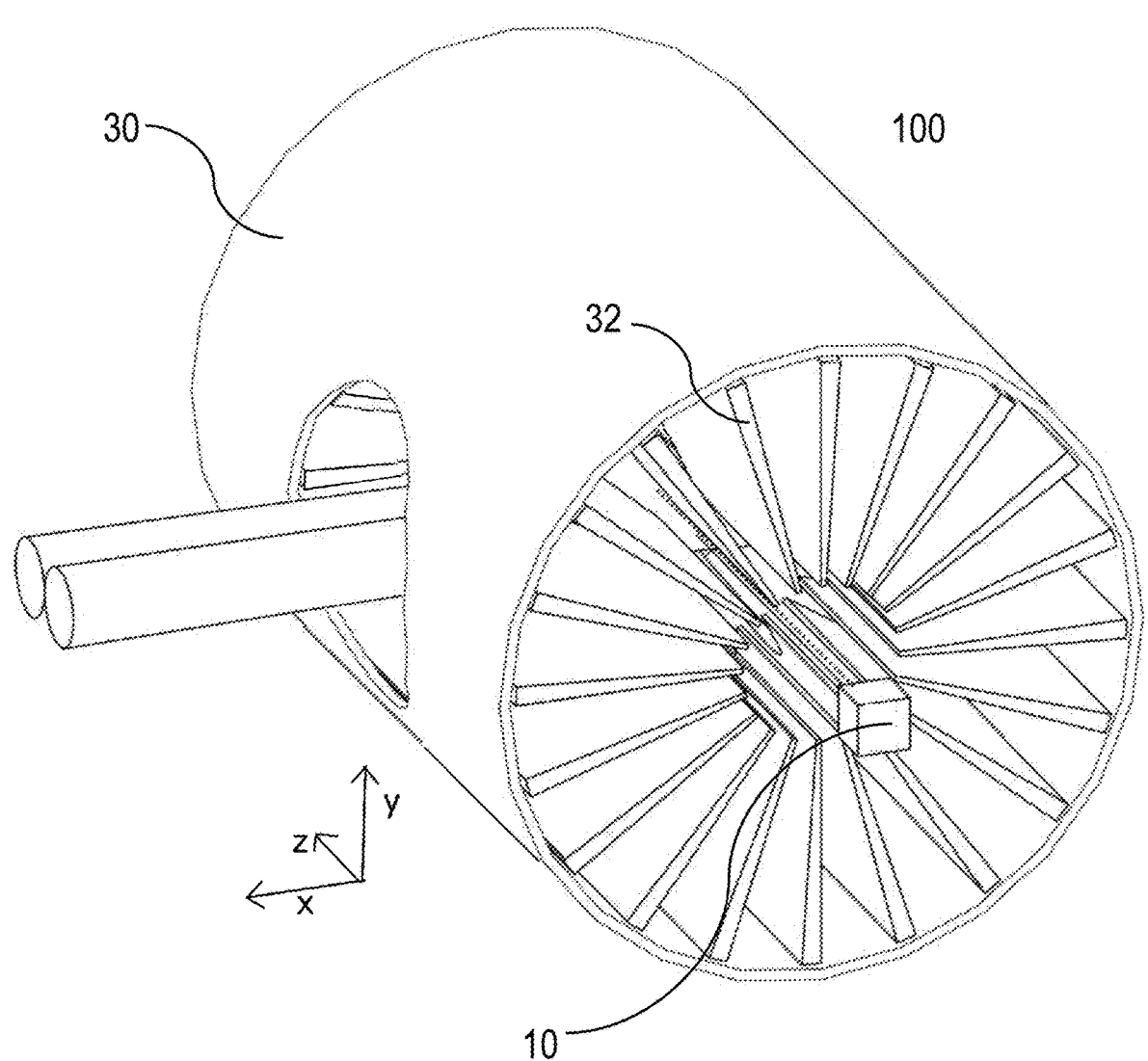
FIGS. 7 to 9: schematic views of preferred embodiments of the X-ray fluorescence measuring apparatus according to the invention with an arrangement of detector elements on a cylindrical surface.
Figure 8:
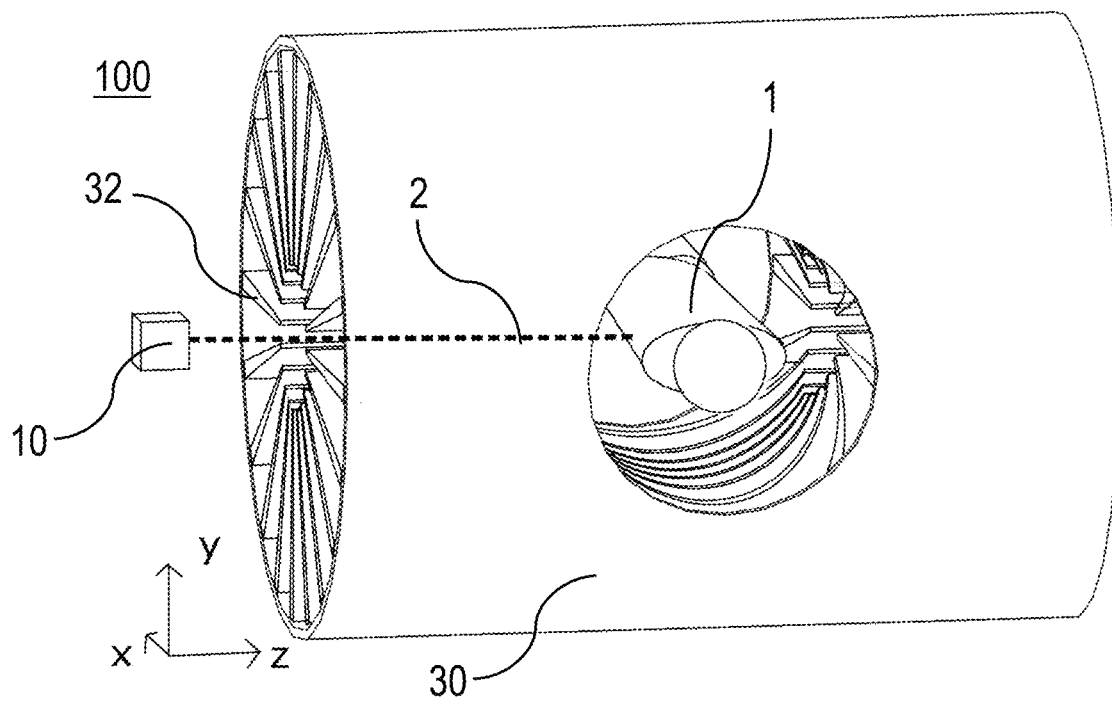
Figure 9:
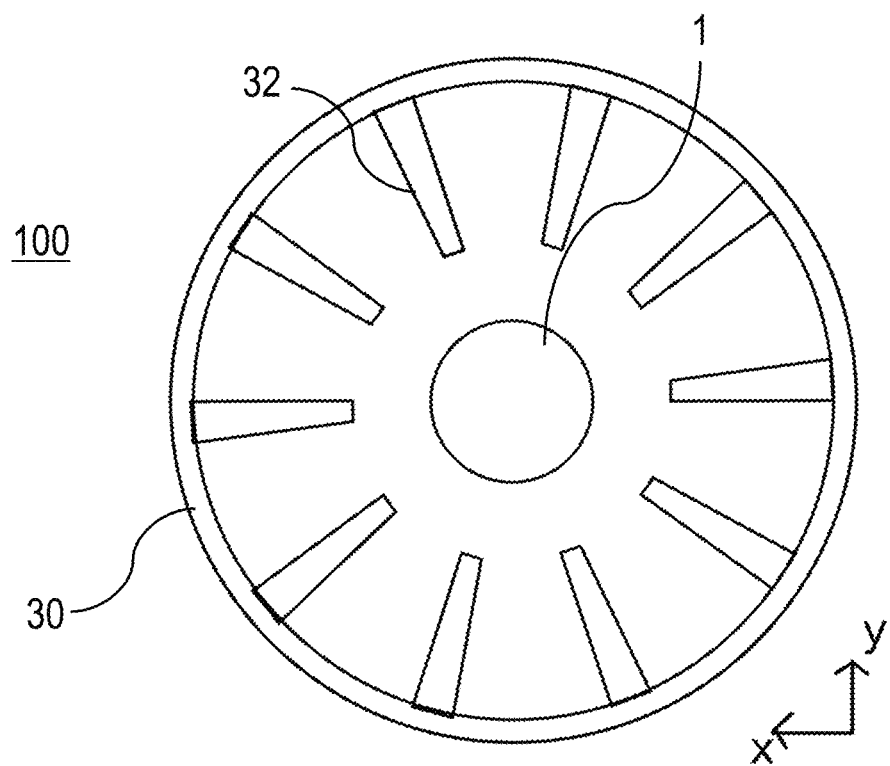

FIGS. 7 to 9 show schematically various perspectives of the X-ray fluorescence measuring apparatus 100 with an arrangement of detector elements 31 on a cylindrical surface, whereby detector elements on flat end faces of the cylinder are not shown. The object is enclosed almost completely by the detector elements. Alternatively a detection can be provided in a half-space in forward direction of the X-ray beam (not represented). In FIGS. 7 to 9 the holding device, the scanning device, the control device and the swivel device are not shown, but are provided as represented in FIG. 1.

The X-ray fluorescence measurement according to the invention is carried out on an object 1, into which a solution containing the target particles has been injected beforehand. The object 1 is introduced into the X-ray fluorescence measuring apparatus 100, such that the X-ray beam 2 can be directed onto an interesting part of the object 1. The source device 10 is actuated and the X-ray beam 2 is scanned over the object 1 with the scanning device 20. The X-ray radiation emitted from the object in a plurality of spatial directions is detected with the detector array device 30. Detector signals are received and processed with the control device 40, as explained below and shown in the flowcharts of FIGS. 10 and 11.

The X-ray fluorescence measurement according to the invention is based more particularly on the following considerations of the inventors. Apart from knowledge of the direction dependence or anisotropy of the background two essential requirements are fulfilled by the method:
(1) The method is not to presuppose a priori knowledge of the position of the target particles along the scanning X-ray beam 2. Conventional XRF imaging methods presuppose this however, as a result of which scanning must be performed multiple times (simply because one does not know at the time where the patient's tumor is situated) and therefore the dose is significantly higher; and
(2) The multiple Compton scattering is to be reduced to the maximum extent. Simply Compton-scattered photons cannot be blocked, because they come from the same area as the fluorescence photons.

Requirement (1) rules out collimators and/or measuring methods (such as e.g. in DE 10 2012 023 344 A1) that allow only a restricted viewing volume along the scanning beam. Many other methods use this restriction nonetheless, as this can reduce the background considerably but equally weakens the signal too much, such that the sensitivity cannot become maximal. Requirement (2) however allows such collimators, which of course do not cut the needle beam volume, but block all areas outside the beam volume maximally.

Both requirements can be fulfilled by the radial screen lamellas 32 being arranged along the scanning X-ray beam 2. These do not restrict the view of the whole beam volume, but block photons that have been scattered once again outside the beam volume.

Figure 12:
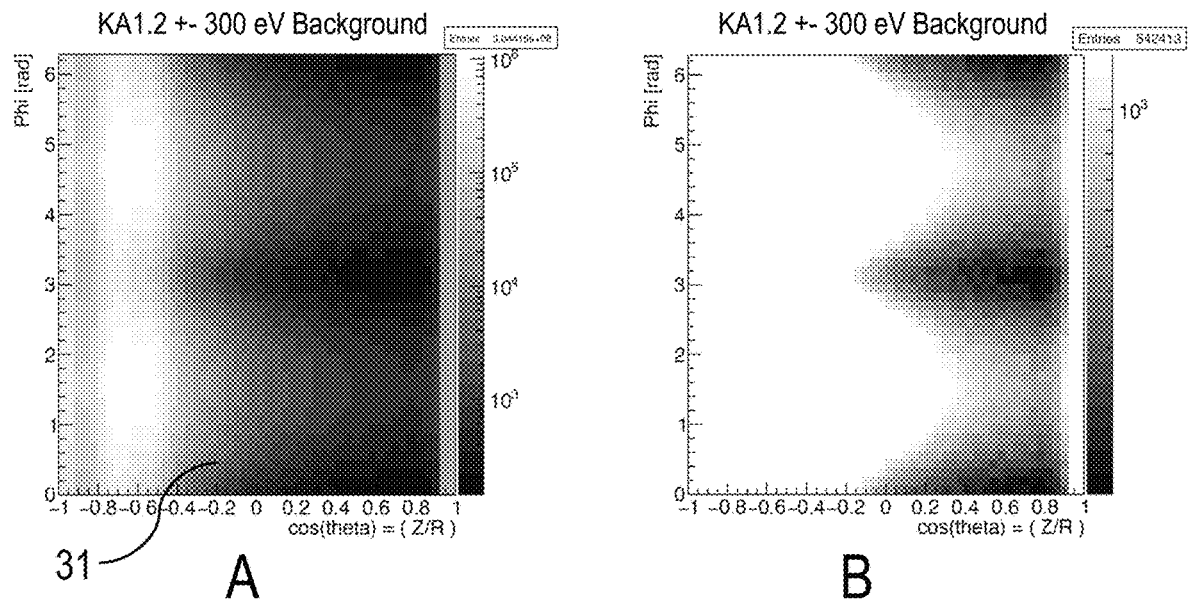
FIG. 12: a graphic illustration of the selection of significant detector elements.
Figure 13:
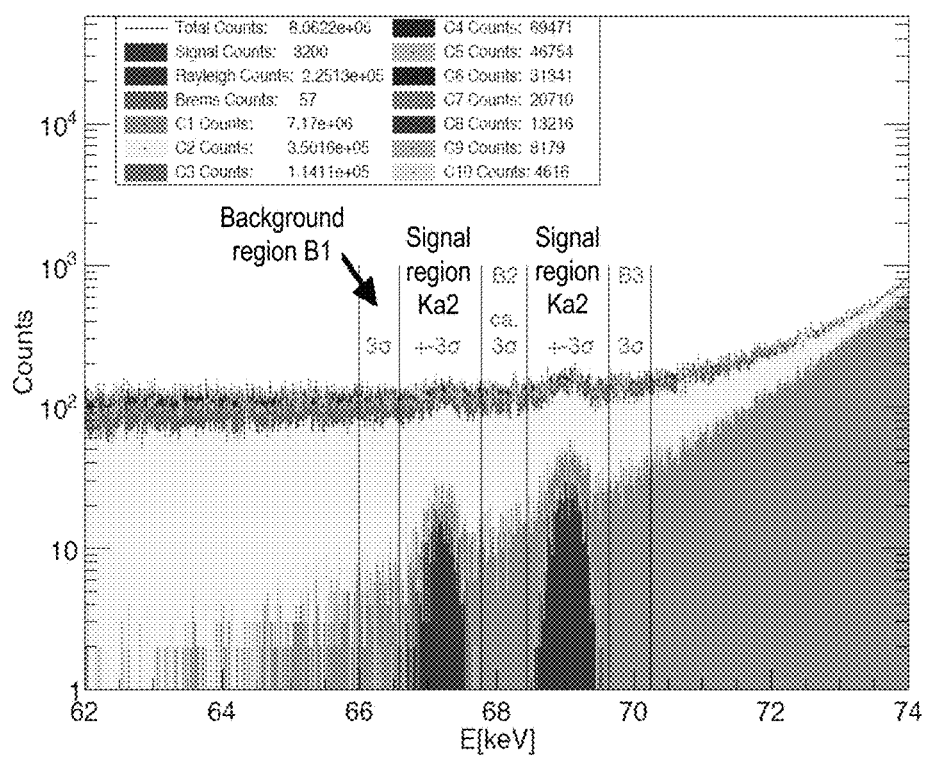
FIG. 13: a graphic illustration of the spectral sum signal at a target scan position.

The essential gain in background reduction, e.g. by the factor 570, is achieved by means of the so-called "spatial filtering" of the detector signals, as described above, i.e. through the identification of a subset of all existing detector elements, after a first background reduction exists owing to the screen lamellas 32. This method is based on the anisotropy of the background illustrated in FIG. 12 (see also FIG. 14). FIG. 12 shows schematically a developed view of the detector elements 31 and the detector elements 31 taken into account in signal processing in a conventional method (FIG. 12A) and by way of example in the method according to the invention (FIG. 12B). The identification of the selected detector elements 31 is based on the following considerations.
(1) Each detector element (or pixel) 31 (e.g. on a cylindrical surface along the beam direction around the object 1) is its own detector with a certain energy resolution, i.e. each pixel measures an energy spectrum.
(2) Each of the detector elements 31 has inputs of both signal and background photons. In this connection the signal photons can be emitted and detected from all sites inside the beam volume. In order for XRF imaging to be able to function also in respect of patients, i.e. for a still high sensitivity to be made possible also in large objects, the background must be reduced far more than in existing methods without decreasing the number of the signal photons excessively.
(3) The background reduction according to the invention is based on a pixel selection, such that no longer are all pixels read, but only certain ones. If one reads too many (or even all) pixels, so much background is detected, that the signal photons are completely masked. If in contrast one reads only very few pixels, the background might well be reduced, but so will the signal also. The method according to the invention leads close to or even into a clear optimum by discarding iteratively from the signal processing in each case precisely that pixel, the removal of which increases the significance of the sum signal of the remaining pixels. The method of pixel selection terminates, when the next pixel to be removed brings no further increase in significance. Then the situation in FIG. 12B is reached: the sum spectrum of the still present pixels has the maximum signal significance, as a result of which one has reached a signal curve, as shown by way of example in FIG. 13, i.e. the fluorescence signal is now perceptible.

Figure 10:
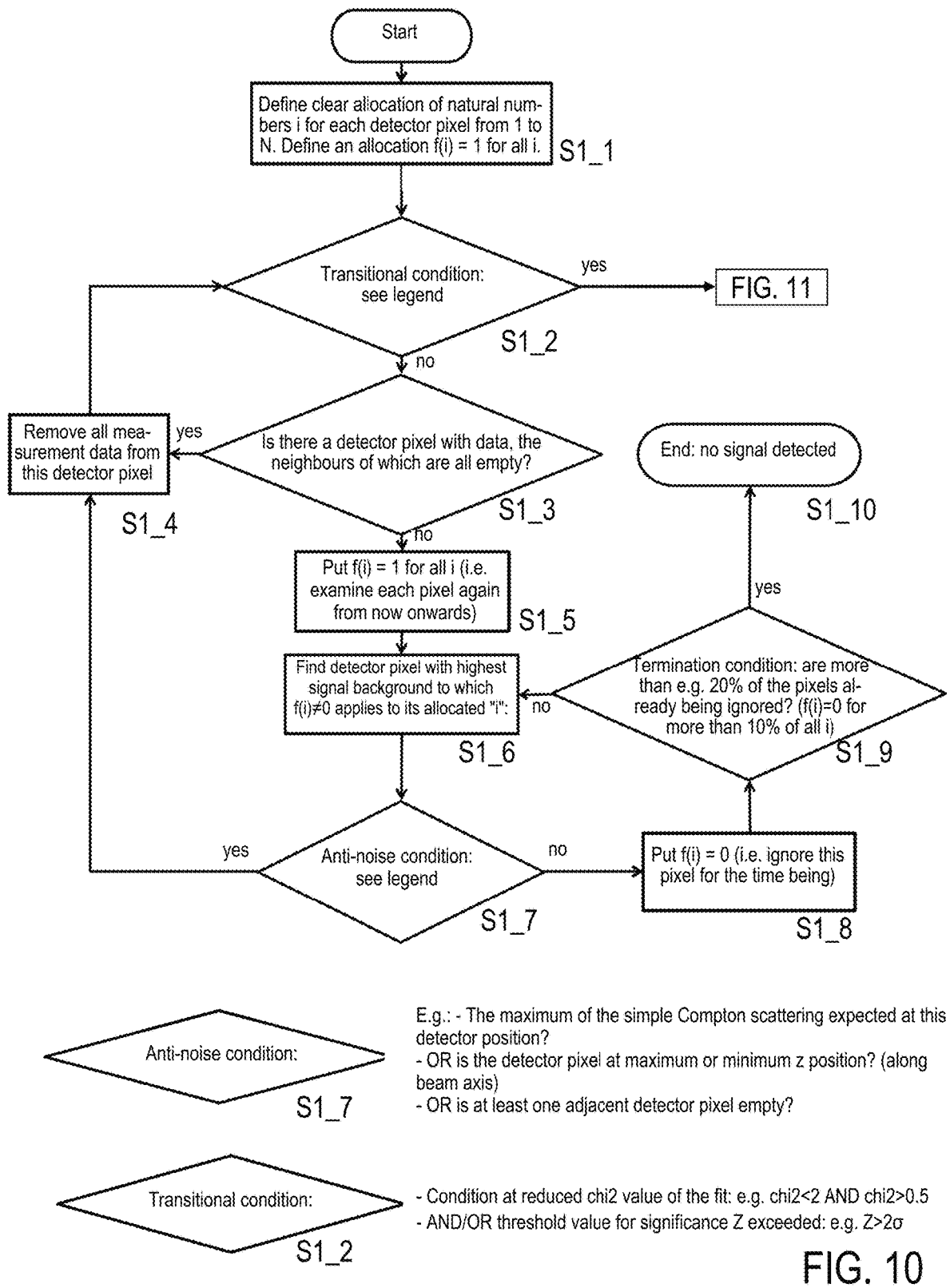
FIGS. 10 and 11: flowcharts to illustrate features of preferred embodiments of the method according to the invention.
Figure 11:
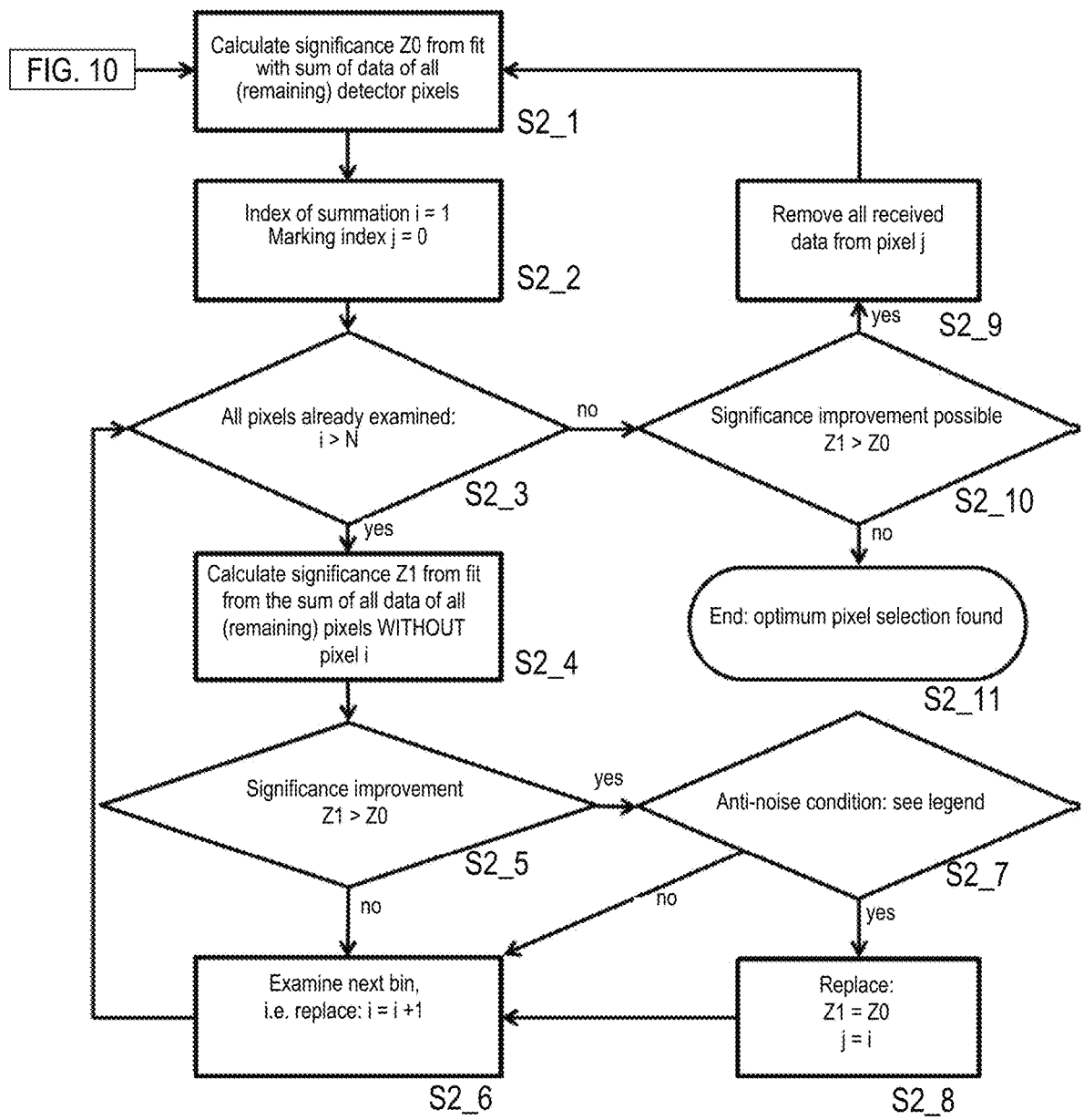

FIGS. 10 and 11 show the two-stage variant of the identification of the significant detector elements, wherein in a first selection step (FIG. 10, background-based pixel selection without fit) detector elements are discarded, which detect predominantly background X-ray scatter radiation, and in a second selection step (FIG. 11, significance-based pixel selection with fit) further detector elements are discarded, the detection signals of which do not deliver any increase of the statistical significance of a sum signal of the remaining detector elements. Alternatively the performance of the identification of the significant detector elements can be limited to the method according to FIG. 10.

Before the identification of the significant detector elements the needle X-ray beam 2 scans the object 1 along the transversal cross-section, whereby each step is called scan position. Therefore all positions in the projection plane of the object 1 are covered. The X-ray beam 2 meets the projection plane perpendicularly.

Thereafter the identified detector elements are selected for each scan position individually (this can take place in parallel with the detections or thereafter; i.e. data are stored during the detections from all detector elements):

If a fluorescence signal is present, i.e. the two gold fluorescence lines (see FIG. 13), these are separated from one another in the energy spectrum of the sum signal of the considered detector elements by a pure background region and on the left and right of the signal regions there are likewise background regions (see FIG. 13): in the background region there can be only background photons and no signal photons. These regions are therefore a reference value. If there is no fluorescence signal, the signal regions would not differ significantly statistically from the background regions.

With steps S1_3 to S1_7 the method according to FIG. 10 discards detector elements from further consideration (i.e. ignores the detected energy spectra of these pixels), until the inputs in the three background regions B1, B2 and B3 (FIG. 13) have been reduced so much, that—if present—the statistical significance of the background rise in the two signal regions exceeds a value of e.g. ≥2 (test in step S1_2).

Were no signal to be present, this termination criterion would never be reached and the algorithm stops at the last remaining pixel (or when e.g. 80% of all pixels have already been discarded) (step S1_10).

If the test is fulfilled in step S1_2 (transitional condition), the second algorithm is now started (FIG. 11): here for the further pixel selection all spectra of the still remaining pixels are added up into a sum spectrum and the significance of the signal is determined directly through fit functions by way of the two signal regions (steps S2_1 to S2_8). The crucial advantage of this algorithm is, that fit functions map the background regions better (in the first step of FIG. 10 the background is assumed to be constant over all regions, which is however only an approximation) and the fluorescence signal can be distinguished from the background by means of the fits, i.e. it is only through the fits that the number of fluorescence photons vs background photons can be determined from the sum spectrum and thus the pixels are discarded, which contribute more to the background than to the signal.

This "fit-based" pixel selection stops, as soon as the next detector element to be removed does not increase further (step S2_10), but reduces the significance (simply because one would remove further background, but from there also too much signal, so one can gain nothing more). As a result in step S2_11 the optimal selection of the identified detector elements is output. Then the scan position, for which the target particles were detected, is output as target scan position.

Thereafter the combination comprising source, detector array and scanning devices 10, 20, 30 is swivelled with the swivel device 60, in order to scan a scanning line according to the target scan position in a second projection plane (x-z plane). The scan position along the scanning line yields the position of the target particles in z direction and thus together with the scan position in the first projection plane the coordinates of the target particles.

Figure 14:
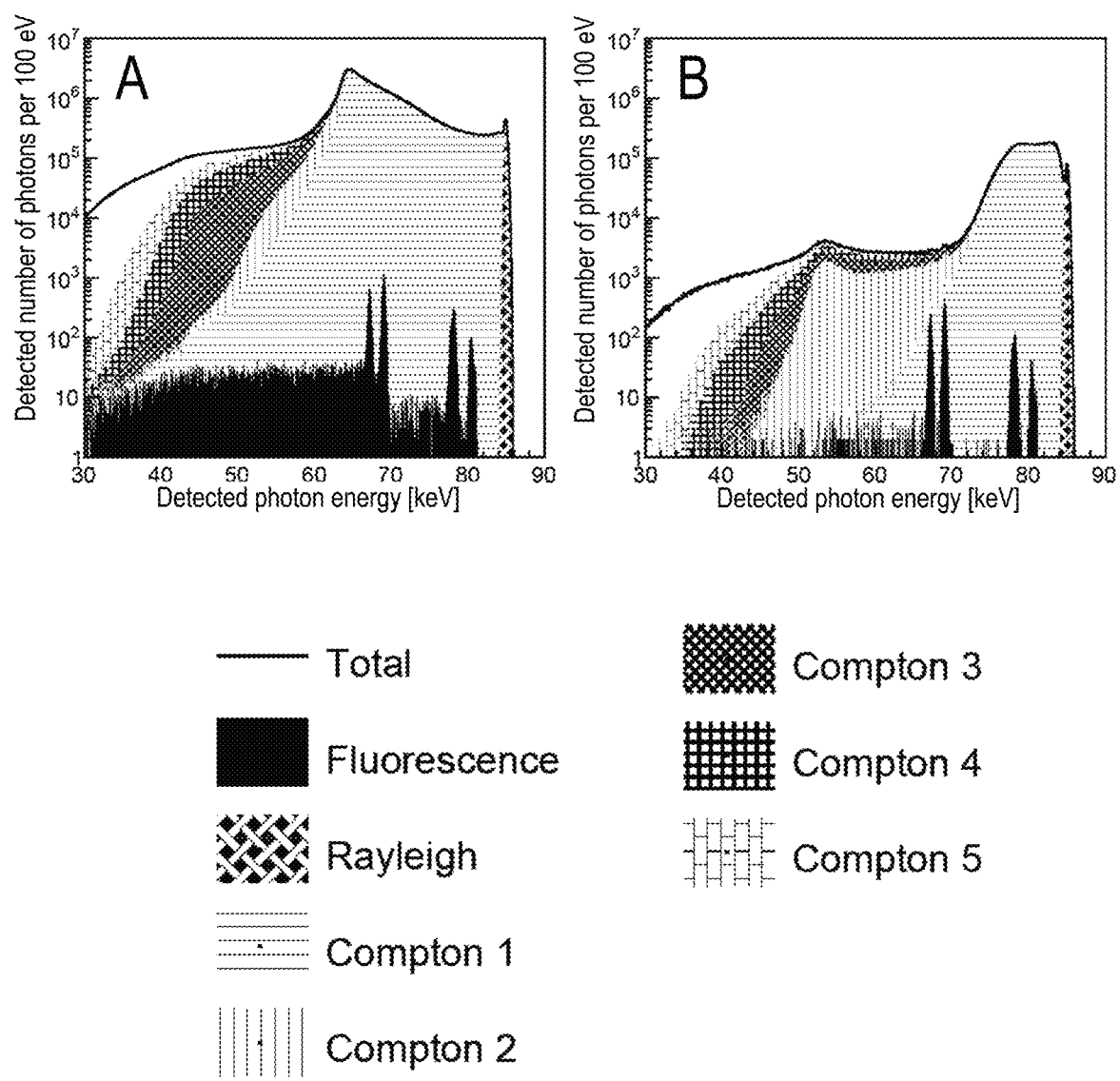
FIG. 14: a graphic illustration of the background suppression achieved according to the invention using the measurable X-ray spectra.

FIG. 14 shows a further demonstration of the advantages of the invention using the simulated X-ray spectra of the detector elements 31, which are shown in FIG. 12. FIG. 14A shows the X-ray spectrum that would be measured, if the collimator is used, but the method according to the invention is not applied (use of all detector elements according to FIG. 12A). The measurement signal is strongly overlaid by the Compton scattering (1 to 5 times). FIG. 14B shows the X-ray spectrum that would be measured according to the invention (use of identified detector elements according to FIG. 12B) and is characterized by a considerable background reduction. The statistical significance of the signal from the two fluorescence lines in FIG. 14B is more than 10 times the standard deviation.

The features of the invention disclosed in the above description, the drawings and the claims can be of importance both individually and also in combination or sub-combination for the realization of the invention in its various embodiments.

The invention claimed is:

1. A method for an X-ray fluorescence measurement, wherein a presence of fluorescing target particles is detected in an object to be examined and target particles that are present are localized in the object, comprising the steps of:
    (a) generating an X-ray beam using a source device, wherein the X-ray beam extends through the object in an X-ray beam direction parallel to a first projection direction,
    (b) irradiating the object with the X-ray beam at a multiplicity of scan positions in a first projection plane, wherein the multiplicity of scan positions are set by a scanning device, by way of which the source device and the object are moved relative to one another,
    (c) detecting X-ray radiation, emitted from the object in a plurality of spatial directions, at each scan position of the multiplicity of scan positions using a detector array device, which is securely connected to the source device, wherein the detector array device comprises a multiplicity of spectrally selective detector elements, which are arranged to detect the X-ray radiation in the plurality of spatial directions, and a plurality of screen lamellas, which extend in radial directions relative to the X-ray beam direction, which shield the multiplicity of spectrally selective detector elements from X-ray radiation scattered in the object and which are arranged in such a way that the multiplicity of spectrally selective detector elements are able to detect X-ray radiation from all locations within a volume of the X-ray beam in the object, wherein the step of detecting the X-ray radiation includes measuring an energy spectrum of the X-ray radiation emitted from the object with each detector element for each of the multiplicity of scan positions, and
    (d) processing detector signals of the multiplicity of spectrally selective detector elements in order to detect X-ray fluorescence of target particles in the detected X-ray radiation and in order to localize the target particles in the object if the X-ray fluorescence is detected, wherein:
    the step of processing detector signals includes selecting a subset of significant detector elements among said multiplicity of spectrally selective detector elements, wherein said subset of significant detector elements facilitates detection of the X-ray fluorescence of the target particles and has detector signals with a statistical significance that is increased in comparison with remaining detector elements of the multiplicity of spectrally selective detector elements, which are not significant detector elements, wherein for each of the multiplicity of scan positions, the subset of the significant detector elements is selected in such a way that: (i) the detector signals of the significant detector elements facilitate the detection of the X-ray fluorescence of the target particles with a maximum statistical significance or (ii) the detector signals of the remaining detector elements of the multiplicity of spectrally selective detector elements, which are not significant detector elements, are discarded when the detector signals thereof do not deliver any elevation of a statistical significance of a sum signal of the subset of the significant detector elements of the multiplicity of detector elements, and
    detecting the presence of the target particles at at least one scan position of the multiplicity of scan positions and establishing the at least one scan position as a target scan position when significant detector elements are found at the at least one scan position at which the target particles are localized in the first projection plane, and a presence of target particles is not detected when significant detector elements are not found at the at least one scan position.

2. The method according to claim 1, further comprising:
selecting the subset of significant detector elements for each of the multiplicity of scan positions with a two-stage selection, wherein the two-stage selection comprises:

discarding detector elements of the multiplicity of detector elements which detect predominantly background X-ray scatter radiation, and discarding further detector elements of the multiplicity of detector elements, the detector signals of which do not deliver any increase of the statistical significance of a sum signal of the already selected detector elements of the multiplicity of detector elements.

3. The method according to claim 1, further comprising establishing a preselected subset of detector elements on a basis of a priori information about the object being examined and selecting the subset of significant detector elements in the preselected subset of detector elements for each of the multiplicity of predetermined scan positions.

4. The method according to claim 1, wherein:

performing the steps a to d in a preparatory measurement with a first X-ray beam with a first diameter, in order to establish a preparatory target scan position representing a target scan region in the first projection plane when the presence of the target particles is detected, and thereafter performing the steps a to d in a main measurement with a second X-ray beam with a second diameter, which is the same as the first diameter or smaller than the first diameter, whereby a selected target scan position is established inside the target scan region.

5. The method according to claim 1, comprising at least one of the features:

the detector array device comprises an arrangement of the multiplicity of spectrally selective detector elements on a surface that covers a half-space in forward direction of the X-ray beam, and the detector array device comprises an arrangement of the multiplicity of spectrally selective detector elements on a spherical surface or a cylindrical surface.

6. The method according to claim 1, wherein when at least one target scan position is established, the method further comprises the steps of:

swivelling of the source and detector array devices in such a way that the X-ray beam extends parallel to a second projection direction, which deviates from the first projection direction, irradiating of the object with the X-ray beam at a multiplicity of scan positions along a scanning line in a second projection plane, which deviates from the first projection plane, whereby the scanning line contains the target scan position, and detecting of a position of the target particles along the scanning line.

7. The method according to claim 1, further comprising the step of collecting of at least one absorption projection image of the object.

8. The method according to claim 1, comprising at least one of the features:

the object is a human test subject, and the target particles contain atoms with a mass number in a range of mass numbers of iodine to gold and are functionalized with a marker substance or medications.

9. The method according to claim 6, wherein the swivelling of the source and detector array devices takes place in such a way that the second projection direction is orientated perpendicular to the first projection direction and the second projection plane is orientated perpendicular to the first projection plane.

10. An X-ray fluorescence measuring apparatus, which is configured to localize fluorescing target particles in an object to be examined, comprising:

a holding device, which is configured to accommodate the object, a source device, which is configured to generate an X-ray beam, which extends through the object to be examined in an X-ray beam direction parallel to a first projection direction, a detector array device, which is securely connected to the source device, is configured to detect X-ray radiation, emitted from the object in a plurality of spatial directions, a multiplicity of spectrally selective detector elements, which are arranged to detect the X-ray radiation in the plurality of spatial directions, and a plurality of screen lamellas, which extend in radial directions relative to the X-ray beam direction, which shield the detector elements from X-ray radiation scattered in the object and which are arranged in such a way that the detector elements are able to detect X-ray radiation from all locations within a volume of the X-ray beam in the object, a scanning device, by use of which the source and detector array devices and the holding device can be moved relative to one another in such a way that the X-ray beam can scan the object in a first projection plane at a multiplicity of scan positions, and a control device, which is configured to process detector signals of the detector elements, in order to detect X-ray fluorescence of target particles in the detected X-ray radiation and in order to localize the target particles in the object if the X-ray fluorescence is detected, wherein:

the control device is configured to select a subset of significant detector elements for each of a multiplicity of scan positions, the detector signals of said significant detector elements facilitating the detection of the X-ray fluorescence of the target particles with a statistical significance that is increased in comparison with remaining detector elements of the multiplicity of detector elements, which are not significant detector elements, and detecting the presence of the target particles at at least one of the multiplicity of scan positions and establishing the at least one scan position as a target scan position when significant detector elements are found at the at least one scan position at which the target particles are localized in the first projection plane, and the presence of target particles is not detected when significant detector elements are not found at the at least one of the multiplicity of scan positions, and the control device is configured to select the subset of significant detector elements, such that: (i) the detector signals of said significant detector elements facilitate the detection of the X-ray fluorescence of the target particles with a maximum statistical significance or (ii) the detector signals of the remaining detector elements of the multiplicity of detector elements, which are not significant detector elements, are discarded when the detector signals thereof do not deliver any increase of the statistical significance of a sum signal of the subset of the significant detector elements of the multiplicity of detector elements.

11. The X-ray fluorescence measuring apparatus according claim 10, wherein:

the control device is configured to select the subset of significant detector elements based on a two-stage selection, wherein the two-stage selection comprises:

discarding detector elements of the multiplicity of detector elements which detect predominantly background X-ray scatter radiation, and discarding further detector elements of the multiplicity of detector elements, the detector signals of which do not deliver any elevation of the statistical significance of a sum signal of the multiplicity of detector elements.

12. The X-ray fluorescence measuring apparatus according to claim 10, comprising at least one of the features:

the detector array device comprises an arrangement of the detector elements on a surface that covers a half-space in a forward direction of the X-ray beam, and the detector array device comprises an arrangement of the detector elements on a spherical surface or a cylindrical surface.

13. The X-ray fluorescence measuring apparatus according to claim 10, comprising:

a swivel device configured to be attached to the source and detector array devices and configured to swivel the source and detector array devices, such that the X-ray beam extends parallel to a second projection direction, which deviates from the first projection direction, wherein:

the scanning device is configured for a movement of the source and detector array devices and of the holding device relative to one another in such a way that the X-ray beam can scan the object along a scanning line in a second projection plane, which deviates from the first projection plane, and the control device is configured to detect the position of the target particles along the scanning line when at least one target scan position has been established.

14. The X-ray fluorescence measuring apparatus according to claim 10, wherein the detector array device and the control device are configured to take at least one absorption projection image of the object.

15. The X-ray fluorescence measuring apparatus according to claim 13, wherein the swivel device, with which the source and detector array devices are swivellable, is configured in such a way that the second projection direction is orientated perpendicular to the first projection direction and the second projection plane is orientated perpendicular to the first projection plane.

* * * * *